(12) United States Patent
Lorenzo

(10) Patent No.: US 10,792,054 B1
(45) Date of Patent: Oct. 6, 2020

(54) CATHETER FOR THROMBOEMBOLIC DISEASE WITH MECHANIC WAVES, INJECTION AND EJECTION

(71) Applicant: Eduardo Lorenzo, Pembroke Pines, FL (US)

(72) Inventor: Eduardo Lorenzo, Pembroke Pines, FL (US)

( * ) Notice: Subject to any disclaimer, the term of this patent is extended or adjusted under 35 U.S.C. 154(b) by 0 days.

(21) Appl. No.: 16/838,826

(22) Filed: Apr. 2, 2020

Related U.S. Application Data

(60) Provisional application No. 62/921,846, filed on Jul. 11, 2019.

(51) Int. Cl.
*A61B 17/22* (2006.01)
*A61M 25/00* (2006.01)

(52) U.S. Cl.
CPC .......... *A61B 17/22012* (2013.01); *A61B 2017/22079* (2013.01); *A61B 2017/22081* (2013.01); *A61M 25/0032* (2013.01); *A61M 2025/0037* (2013.01)

(58) Field of Classification Search
CPC .... A61B 17/22012; A61B 2017/22025; A61B 17/2202; A61B 2017/22021; A61B 17/22022; A61M 25/0026; A61M 25/0032; A61M 2025/0039; A61M 2025/004
See application file for complete search history.

(56) References Cited

U.S. PATENT DOCUMENTS

| | | |
|---|---|---|
| 5,447,509 A | 9/1995 | Mills et al. |
| 6,312,444 B1 | 11/2001 | Barbut |
| 6,936,025 B1 | 8/2005 | Evans et al. |
| 8,241,241 B2 | 8/2012 | Evans et al. |
| 8,460,312 B2 | 6/2013 | Bose et al. |
| 8,535,290 B2 | 9/2013 | Evans et al. |
| 8,784,441 B2 | 7/2014 | Rosenbluth et al. |
| 9,161,768 B2 | 10/2015 | Cioanta et al. |
| 9,375,223 B2 | 6/2016 | Wallace |
| 9,415,187 B2 | 8/2016 | Agnew |
| 9,629,654 B2 | 4/2017 | Andersen |
| 9,655,633 B2 | 5/2017 | Leynov et al. |
| 9,848,975 B2 | 12/2017 | Hauser |
| 9,895,158 B2 | 2/2018 | Dixon et al. |
| 10,016,266 B2 | 7/2018 | Hauser |
| 10,182,834 B2 | 1/2019 | Merk et al. |
| 10,188,409 B2 | 1/2019 | Smalling |
| 10,192,230 B2 | 1/2019 | Look et al. |

(Continued)

FOREIGN PATENT DOCUMENTS

| | | |
|---|---|---|
| CA | 2439667 A1 | 3/2005 |
| CA | 3050858 A1 | 8/2018 |

(Continued)

*Primary Examiner* — Wade Miles
(74) *Attorney, Agent, or Firm* — Albert Bordas, P.A.

(57) ABSTRACT

A catheter for thromboembolic disease with mechanic waves, injection, and ejection having a triple-lumen catheter system, whereby a first lumen is for injection, a second lumen is for ejection, and a third lumen has a mechanical wave emitter for wave emissions. The first lumen, the second lumen, and the third lumen are longitudinal, whereby the first lumen and the second lumen are symmetrical and opposite each other, and the third lumen is positioned approximately at a center of the triple lumen catheter system.

8 Claims, 4 Drawing Sheets

(56) References Cited

U.S. PATENT DOCUMENTS

| | | | |
|---|---|---|---|
| 2006/0047239 A1* | 3/2006 | Nita | A61B 17/2251 |
| | | | 604/22 |
| 2009/0187137 A1 | 7/2009 | Volz et al. | |
| 2013/0281897 A1 | 10/2013 | Hoffmann | |
| 2014/0336665 A1* | 11/2014 | Gavala | A61B 17/22012 |
| | | | 606/128 |
| 2017/0215965 A1* | 8/2017 | Harrah | A61M 25/003 |
| 2018/0206867 A1 | 7/2018 | Allen | |
| 2019/0150703 A1* | 5/2019 | Baker | A61B 1/307 |
| 2019/0209198 A1* | 7/2019 | Song | A61B 18/00 |

FOREIGN PATENT DOCUMENTS

| | | |
|---|---|---|
| CN | 103212148 A | 8/2015 |
| CN | 105361923 A | 8/2018 |
| GB | 2429158 A | 10/2007 |
| JP | 2018514355 A | 6/2018 |
| KR | 20190035792 A | 4/2019 |
| KR | 20190075097 A | 6/2019 |
| WO | 2003099100 A2 | 11/2004 |
| WO | 2009152352 A2 | 12/2010 |
| WO | 2018014021 A2 | 1/2018 |
| WO | 2018083666 A1 | 5/2018 |
| WO | 2019111239 A1 | 6/2019 |

* cited by examiner

CATHETER FOR THROMBOEMBOLIC DISEASE WITH MECHANIC WAVES, INJECTION AND EJECTION

BACKGROUND OF THE INVENTION

1. Field of the Invention

The present invention relates to medical devices, and more particularly, to catheters for thromboembolic diseases, which have combined mechanic waves, injection, and ejection functions.

2. Description of the Related Art

Applicant believes that one of the closest references corresponds to U.S. Pat. No. 5,447,509 A issued to Mills, et al. on Sep. 5, 1995 for Ultrasound catheter system having modulated output with feedback control. However, it differs from the present invention because Mills, et al. teach a method and apparatus for driving an ultrasound transducer coupled to an ultrasound transmission disposed within an elongate catheter that has a modulated output and utilizes feedback control. A modulating signal varying in amplitude and continuous in duration modulates an ultrasound transducer drive signal. The resulting modulated ultrasound transducer drive signal is likewise continuous in duration such that it lacks the abrupt accelerations which cause stress to be applied to the ultrasound transmission member in prior art devices. The current of the modulated drive signal is monitored and the voltage thereof is varied in response to changes in the current in order to provide feedback control. A transmission member breakage alarm provides an indication of transmission member breakage in the event that any comparison of the drive energy to the feedback control signal indicates that the desired ultrasonic vibration has been reached at a drive energy level less than the minimum drive energy level typically desired for such desired ultrasound vibration when the ultrasound transmission member is intact.

Applicant believes that another reference corresponds to U.S. Pat. No. 6,312,444 B1 issued to Barbut on Nov. 6, 2001 for Medical device for removing thromboembolic material from cerebral arteries and methods of use. However, it differs from the present invention because Barbut teaches a medical device having an elongate catheter, a balloon occluder mounted on a distal end of the catheter, and optionally a chopping mechanism associated with an aspiration port of the catheter. Continuous or intermittent suction can be applied to the aspiration port, which is distal to the occluder to dislodge thromboembolic material in a carotid or cerebral artery. Oxygenated blood or other fluid, which may be hypothermic, can be perfused through at least one perfusion port proximal to the occluder to maintain and augment perfusion of the collateral vasculature proximal to the occlusive lesion. The flow rate of blood or fluid can be controlled by rotating two cylindrical members. Neuroprotective agents or t-PA can also be infused distal to the occluder through the aspiration port or an infusing port.

Applicant believes that another reference corresponds to U.S. Pat. No. 6,936,025 B1 issued to Evans, et al. on Aug. 30, 2005 for Thrombolysis device. However, it differs from the present invention because Evans, et al. teach a catheter suitable for dissolving blockages in tubular tissue, which provides a combination of low frequency (1-100 Hz) vibratory motion and injection of a lysing agent. The tubular tissue may be veins, arteries, ducts, intestines, or any other blocked body lumen. For vascular thrombi, the catheter may induce a vibrating, stirring action in and around the thrombus in combination with dispensing of a thrombolytic agent, such as urokinase, into the thrombus. An inflatable or expandable member may be provided near a distal tip of the catheter to prevent release of dislodged thrombus.

Applicant believes that another reference corresponds to U.S. Pat. No. 8,241,241 B2 issued to Evans, et al. on Aug. 14, 2012 for Apparatus and methods for clot dissolution. However, it differs from the present invention because Evans, et al. teach a catheter having the ability to infuse a thrombolytic agent, aspirate clot and fluid, and allow passage of a guidewire. Optionally, the catheter may also include a mechanical agitator for further disrupt clot in the presence of the thrombolytic agent. A flow resistor in the catheter provides for infusion and/or aspiration to be concentrated primarily at a clot treatment area in a blood vessel while also providing optional infusion and/or aspiration distal to the treatment area. In some embodiments, infusion, aspiration and guidewire passage occur through a common lumen. The thrombolytic agent, such as tPA, streptokinase, or urokinase, is directly released into the clot at the point where the agitator is engaging the clot. In this way, the thrombolytic activity of the agent is enhanced and the dissolution of the clot is improved.

Applicant believes that another reference corresponds to U.S. Pat. No. 8,460,312 B2 issued to Bose, et al. on Jun. 11, 2013 for System and method for treating ischemic stroke. However, it differs from the present invention because Bose, et al. teach a thromboembolic removal system for treating ischemic stroke, including a guide and occlusion catheter, a delivery and aspiration catheter, an aspiration pump, a thromboembolic receiver, and a thromboembolic separator.

Applicant believes that another reference corresponds to U.S. Pat. No. 8,535,290 B2 issued to Evans, et al. on Sep. 17, 2013 for Apparatus and methods for clot dissolution. However, it differs from the present invention because Evans, et al. teach a catheter having the ability to infuse a thrombolytic agent, aspirate clot and fluid, and allow passage of a guidewire. Optionally, the catheter may also include a mechanical agitator for further disrupt clot in the presence of the thrombolytic agent. A flow resistor in the catheter provides for infusion and/or aspiration to be concentrated primarily at a clot treatment area in a blood vessel while also providing optional infusion and/or aspiration distal to the treatment area. In some embodiments, infusion, aspiration, and guidewire passage occur through a common lumen. The thrombolytic agent, such as, tPA, streptokinase, or urokinase, is directly released into the clot at the point where the agitator is engaging the clot. In this way, the thrombolytic activity of the agent is enhanced and the dissolution of the clot is improved.

Applicant believes that another reference corresponds to U.S. Pat. No. 8,784,441 B2 issued to Rosenbluth, et al. on Jul. 22, 2014 for Embolectomy catheters and methods for treating stroke and other small vessel thromboembolic disorders. However, it differs from the present invention because Rosenbluth, et al. teach an embolectomy catheters, rapid exchange microcatheters, systems and methods for removing clots or other obstructive matter from blood vessels. The embolectomy catheters are advanceable with or over a guidewire, which has been pre-inserted through or around the clot. Also, in some embodiments, the embolectomy catheters include clot removal devices, which are deployable from the catheter after the catheter has been advanced at least partially through the clot. The clot removal device may include a deployable wire nest that is designed to prevent a blood clot from passing therethrough. The delivery catheter may include telescoping inner and outer tubes, with the clot removal device being radially constrained by the outer tube. Retraction of the outer tube removes the constraint on the clot removal device and permits it to expand to its deployed configuration. An infusion guidewire is particularly useful in conjunction with the embolectomy catheter, and permits infusion of medicaments or visualization fluids distal to the clot.

Applicant believes that another reference corresponds to U.S. Pat. No. 9,161,768 B2 issued to Cioanta, et al. on Oct. 20, 2015 for Extracorporeal pressure shock wave devices with reversed applicators and methods for using these devices. However, it differs from the present invention because Cioanta, et al. teach a shock wave applicator that includes a reflector and a shock wave generator disposed in the reflector at a first focal point. The reflector is at least a portion of an ellipsoidal shape having a long and small axis with the first focal point and a second focal point on a long axis, and the reflector terminates at an edge defining a membrane covered-aperture on plane intersecting the small axis and coincident with the second focal point.

Applicant believes that another reference corresponds to U.S. Pat. No. 9,375,223 B2 issued to Wallace on Jun. 28, 2016 for Methods and devices for endovascular therapy. However, it differs from the present invention because Wallace teaches methods and devices for treating endovascular disease. Vibrational energy is delivered to change compliance and increase permeability at the treatment area. To improve clinical outcomes, one or more therapeutic drugs may be delivered to the treatment area.

Applicant believes that another reference corresponds to U.S. Pat. No. 9,415,187 B2 issued to Agnew on Aug. 16, 2016 for Dialysis catheter. However, it differs from the present invention because Agnew teaches a catheter assembly used for extracorporeal treatment, such as dialysis, of blood, or other body fluid, that includes an outer and inner catheter in a coaxial relationship. A fluid path is provided by a passageway defined between the catheters and a distal end of the outer catheter, and another fluid path is provided through a lumen and a distal end of the inner catheter. A sealing member is coupled to one of the catheters. The member in a first position is configured to permit the distal ends of the catheters to transport fluid, while in a second position the member is configured to inhibit at least one of the distal ends from transporting fluid. The sealing member may include a flared portion for enhance sealing. The sealing member may also have a portion extending outward from the catheters to position the distal ends away from vessel contact.

Applicant believes that another reference corresponds to U.S. Pat. No. 9,629,654 B2 issued to Andersen on Apr. 25, 2017 for Thrombus removal apparatus. However, it differs from the present invention because Andersen teaches a thrombus removal apparatus that includes a catheter having at its distal end a solenoid coil section within which there is disposed a piercing element made of electromagnetic material. Within the solenoid coil section there is provided a solenoid coil, which can be powered to generate an electromagnetic field, which causes the piercing element to reciprocate into and out of the coil section, in practice to pierce into and fragment a thrombus disposed in a patient's vessel. An aspiration unit may be provided for aspirating thrombus fragments into the assembly for removal from the patient's vasculature. The apparatus is able to remove dense thrombus material from within a patient, which cannot be otherwise removed by means of thrombolytic agents.

Applicant believes that another reference corresponds to U.S. Pat. No. 9,655,633 B2 issued to Leynov, et al. on May 23, 2017 for System and method for treating ischemic stroke. However, it differs from the present invention because Leynov, et al. teach a thromboembolic removal system for treating ischemic stroke, including a guide and occlusion catheter, a delivery and aspiration catheter, an aspiration pump, a thromboembolic receiver, and a thromboembolic separator.

Applicant believes that another reference corresponds to U.S. Pat. No. 9,848,975 B2 issued to Hauser on Dec. 26, 2017 for Method of removing a thrombus from a blood vessel. However, it differs from the present invention because Hauser teaches a method for mechanically capturing and removing a thrombus from a blood vessel that includes contacting the thrombus with an inner catheter. A self-expanding body is advanced toward the thrombus, wherein the self-expanding body has a proximal end fixed to a distal end of an elongate catheter. The self-expanding body is preferably made from nickel-titanium and includes a tapered proximal end portion and an open distal end. The self-expanding body preferably has a mesh structure. The self-expanding body is allowed to self-expand in the blood vessel. At least a portion of the thrombus is captured by the self-expanding body and the captured thrombus is then retrieved into a lumen of an aspiration catheter. Negative pressure is applied through the lumen of the aspiration catheter during retrieval of the captured thrombus. A thrombolytic drug may be delivered into the blood vessel before capturing and removing the thrombus.

Applicant believes that another reference corresponds to U.S. Pat. No. 9,895,158 B2 issued to Dixon, et al. on Feb. 20, 2018 for Method and apparatus for accelerated disintegration of blood clot. However, it differs from the present invention because Dixon, et al. teach systems and methods for treating a blood clot that include a catheter to be inserted into a patient. The catheter is used to deliver low stability microbubbles toward the blood clot in the patient. A thrombolytic agent is delivered toward the blood clot, and ultrasonic energy is applied to the microbubbles to vibrate the microbubbles.

Applicant believes that another reference corresponds to U.S. Pat. No. 10,016,266 B2 issued to Hauser on Jul. 10, 2018 for Method of removing a thrombus from a blood vessel. However, it differs from the present invention because Hauser teaches a method for mechanically capturing and removing a thrombus from a blood vessel that includes advancing a guidewire into the thrombus. A self-expanding body is allowed to expand in the blood vessel, wherein the self-expanding body is fixed to a distal end portion of an elongate catheter. The self-expanding body preferably includes a tapered proximal end portion and an open distal end while in the expanded configuration. The self-expanding body forms a mesh structure adapted for allowing blood to pass therethrough. The thrombus is captured by the self-expanding body and then retrieved into an aspiration catheter. Aspiration is preferably applied during and after retrieval of the thrombus into the aspiration catheter. A thrombolytic drug may be delivered into the blood vessel before capturing and retrieving the thrombus. In preferred methods of use, the thrombus is captured and removed for reducing health problems associated with a stroke.

Applicant believes that another reference corresponds to U.S. Pat. No. 10,182,834 B2 issued to Merk, et al. on Jan. 22, 2019 for Delivery of thrombolytic agent through actuation member of thrombus retrieval device. However, it differs from the present invention because Merk, et al. teach a method of treating a thrombus wherein a device is advanced to the vicinity of the thrombus, a thrombolytic agent is applied to the thrombus, and an expandable basket of the device is expanded to capture at least a portion of the thrombus within the expandable basket. The device includes a catheter having a distal portion, a lumen and a plurality of openings on the outer surface of the catheter, through which the thrombolytic agent is supplied. The device further includes a sheath and may include a collar, which assists in expanding the expandable basket as the sheath is moved relative to the catheter.

Applicant believes that another reference corresponds to U.S. Pat. No. 10,188,409 B2 issued to Smalling on Jan. 29, 2019 for Aspiration thrombectomy catheter system and associated methods. However, it differs from the present invention because Smalling teaches an aspiration thrombectomy catheter system that includes an aspirator and an aspiration catheter for insertion in a blood vessel. The catheter has a shaft with a proximal end for connection with the aspirator and a tapering distal end with a tip for insertion in the vessel. A plurality of aspiration ports is arranged in sets along the tapering distal end, for aspirating thrombus from the vessel. At least one aspiration lumens within the shaft conducts thrombus from the vessel, through the aspiration ports, to the aspirator. Variably sized or shaped ports provide differing aspiration vectors for enhanced thrombus removal. The aspiration thrombectomy catheter additionally provides for uniform drug dispersion at a thrombotic area, alone or in combination with aspiration of the thrombus. In the event of an adverse reaction, drug dosage may be easily reduced by aspirating dispersed drugs back into the catheter.

Applicant believes that another reference corresponds to U.S. Pat. No. 10,192,230 B2 issued to Look, et al. on Jan. 29, 2019 for Systems and methods for management of thrombosis. However, it differs from the present invention because Look, et al. teach an aspiration system that includes an elongate tubular member having a lumen, an aspiration catheter configured to be inserted through the lumen of the elongate tubular member, and including a tubular aspiration member having a proximal end, a distal end, and a lumen, and configured to at least partially extend out of the lumen of the elongate tubular member at the distal end of the elongate tubular member; an elongate support member coupled to the tubular aspiration member and extending between a proximal end of the aspiration catheter and the proximal end of the tubular aspiration member; and an annular sealing member coupled to the tubular aspiration member and configured to create a seal against an inner surface of the elongate tubular member, when a vacuum sufficient to cause aspiration is actively applied to the lumen of the elongate tubular member.

Applicant believes that another reference corresponds to U.S. Patent Application Publication No. 2009/0187137 A1, published on Jul. 23, 2009 to Volz, et al. for Ultrasound pulse shaping. However, it differs from the present invention because Volz, et al. teach an ultrasound catheter system comprising a catheter having at least one ultrasonic element; and a control system configured to generate power parameters to drive the ultrasonic element to generate ultrasonic energy. The control system is configured to provide an ultrasonic pulse with a high-pressure gradient with respect to time and/or distance. In another embodiment, a method of enhancing delivery of a therapeutic compound comprising delivering the therapeutic compound to a treatment site in a patient; and exposing the treatment site to an ultrasonic energy generated by an oscillating electrical signal pattern having a rise or fall rate greater than an sinusoidal pattern for the same amplitude and frequency.

Applicant believes that another reference corresponds to U.S. Patent Application Publication No. 2013/0281897 A1, published on Oct. 24, 2013 to Hoffmann for Non-invasive reperfusion system by deformation of remote, superficial arteries at a frequency much greater than the pulse rate. However, it differs from the present invention because Hoffmann teaches systems for assisting clearance of an acutely thrombosed artery substantially surrounded by boney external body surfaces, which are resistant to deformative displacement relative to the thrombosed artery by the application of external percussive force. The method consists of applying targeted, localized, non-invasive, high infrasonic to low sonic frequency vibratory percussion with a serial impact frequency much greater than the pulse rate of a patient being treated, the percussion directed towards a remote, preferably superficial "target vessel" residing palpably close to the skin surface. Marked vessel deformations with resultant blood pressure and flow fluctuations are thereby induced by the percussion within the target vessel, which propagate to the acutely thrombosed artery to provide localized agitation and turbulence to assist thrombolytic and/or IV microbubble delivery and effectiveness in facilitating reperfusion. Preferred apparatus for treatment of ST elevation myocardial infarction, acute ischemic stroke and acute pulmonary embolus are presented.

Applicant believes that another reference corresponds to U.S. Patent Application Publication No. 2018/0206867 A1, published on Jul. 26, 2018 to Gourley Allen for Method for the treatment of thromboembolism. However, it differs from the present invention because Allen teaches a method for the treatment of thromboembolism comprising administering a thrombolytic agent directly to the thromboembolism in the presence of ultrasound. The total dose of thrombolytic agent administered is between 1 and 12 mg and the time over which the total dose is delivered is less than 15 hours.

Applicant believes that another reference corresponds to CA Patent No. 2,439,667 A1 issued to Hoffmann on Mar. 4, 2005 for Low frequency vibration assisted blood perfusion system and apparatus. However, it differs from the present invention because Hoffmann teaches an emergency system for the treatment of a patient experiencing an acute thrombotic vascular occlusion, comprising a non-invasive, vibration device, in conjunction with pharmacological agents, for disrupting and lysing thrombosis, relieving spasm (if associated), and thereby restoring blood perfusion. The vibration device is operable to deliver vibration within the 1-1000 Hz range, at selectable displacement amplitude of 0.1-10 mm. For acute myocardial infarction cases, an operator places an attachment interface comprising a pair of contacts, to bridge the sternum of the patient at the fourth intercostal space. Vibration is initiated at 50 Hz (or any frequency, preferably within the 40-120 Hz range), and adjusts vibration to maximal displacement amplitude deemed tolerable and safe to the patient, concurrently with the administration of thrombolytic agents, or any other form of medical therapy. A synergistic effect is achieved between vibration and medical agents to facilitate the disruption of thrombosis, and restore blood perfusion.

Applicant believes that another reference corresponds to CA Patent No. 3,050,858 A1 issued to Allen on Aug. 2, 2018 for Method for the treatment of thromboembolism. However, it differs from the present invention because Allen teaches a method for the treatment of thromboembolism comprising administering a thrombolytic agent directly to the thromboembolism in the presence of ultrasound. The total dose of thrombolytic agent administered is between 1 and 12 mg and the time over which the total dose is delivered is less than 15 hours.

Applicant believes that another reference corresponds to CN Patent No. 103212148 A issued to He Fan Chen Xudong on Aug. 12, 2015 for Iliofemoral deep venous thrombosis moniliform eccentric sacculus thrombolysis thrombectomy catheter and using method of same. However, it differs from the present invention because Chen teaches a iliofemoral deep venous moniliform eccentric sacculus thrombolytic thrombolysis thrombectomy catheter and a using method of the iliofemoral deep venous thrombosis moniliform eccentric sacculus thrombolysis thrombectomy catheter. The tail end of the catheter is composed of two openings, wherein one is a sacculus catheter opening, and the other one is called a Y valve connector, is a common entrance of a guide wire for guiding and a thrombolysis catheter, and is used by being connected with a Y valve. A catheter end is a two-cavity catheter composed of two catheters in a fusing mode, wherein the two catheters are mutually independent in function, one cavity serves as a sacculus catheter passage, and the other cavity serves as a guide wire and thrombolysis catheter passage. A catheter working part is composed of moniliform eccentric sacculus and a corresponding crack thrombectomy catheter on the other side. Catheter cavities are made of a +PTEE hydrophilic coating. Each part of the sacculus and each part of thrombolysis (with the length of 10-20 cm) can work respectively or simultaneously. Sacculus (with the diameter of 5-20 mm) squeezes thrombectomy. Thrombectomy medicine thrombolysis can be simultaneously filled in the crack catheter on the other side. The crack catheter on the other side can rotate so as to improve thrombolysis thrombectomy effect.

Applicant believes that another reference corresponds to CN Patent No. 105361923 A issued to Saltani, et al. on Feb. 2, 2018 for Method and apparatus for treatment of intracranial hemorrhages. However, it differs from the present invention because Saltani, et al. teach an ultrasound catheter with a lumen for fluid delivery and fluid evacuation, and an ultrasound source is used for the treatment of intracerebral or intraventricular hemorrhages. After the catheter is inserted into a blood clot, a lytic drug can be delivered to the blood clot via the lumen while applying ultrasonic energy to the treatment site. As the blood clot is dissolved, the liquefied blood clot can be removed by evacuation through the lumen.

Applicant believes that another reference corresponds to GB Patent No. 2,429,158 A issued to Hoffmann on Oct. 24, 2007 for A kit for low frequency assisted blood perfusion emergency treatment. However, it differs from the present invention because teaches an emergency system for treatment of a patient experiencing an acute vascular obstruction, employing a non-invasive vibrator, in conjunction with drugs, for disrupting and lysing thrombosis, relieving spasm (if associated), and thereby restoring blood perfusion vibrator is operable in the sonic to infrasonic range 1-1000 Hz, preferably 1-120 Hz, with a displacement of 0.1-15 mm. For acute myocardial infarction cases, a pair of contacts are advantageously placed to bridge the sternum at the fourth intercostal space. Vibration is initiated at 50 Hz (or any frequency, preferably within the 20-120 Hz range), and is ideally adjusted to a maximal amplitude (or force) deemed tolerable and safe to the patient, with the administration of thrombolytic agents or other form of drug therapy. A synergistic effect is achieved between vibration and drugs to facilitate the disruption of thrombosis, relieve spasm, and restore blood perfusion. A kit may be provided including instructions, or teachings relating to how to use the device and drug combination. An oscillation device of the type indicated for emergency use is also provided for treatment of acute stroke.

Applicant believes that another reference corresponds to JP Patent No. 2018514355 A issued to Hoffmann on Jun. 7, 2018 for Method and system for generating mechanical pulses. However, it differs from the present invention because Bruillette teaches a method of generating a mechanical wave, the generating step generating a high-amplitude mechanical pulse, a coupling step coupling the mechanical pulse to the proximal end of the transmission member, the mechanical pulse to the transmission member, a method is described that includes a propagation step for propagating from the proximal end to the distal end and a transmission step for transmitting the mechanical pulse at the distal end. In certain embodiments, elongate flexible transmission members are traditional such as guidewires, microcatheters, catheters, over-the-wire balloons, etc., to facilitate access, guidance, and traversal of vascular occlusions.

Applicant believes that another reference corresponds to KR Patent No. 20190035792 A issued to Braid, et al. on Apr. 3, 2019 for Blood collection system for removing occluded blood clots from blood vessels. However, it differs from the present invention because Braid, et al. teach a system for removing occlusion thrombi from a blood vessel that includes a catheter and an apparatus for generating a pulsed vacuum force to pulsate a pressure gradient at a distal end of the catheter. The pulse generator may be integral with or separate from the vacuum pump. The pulse generator can be applied to the flexible tubing between the proximal end of the catheter and the vacuum pump.

Applicant believes that another reference corresponds to KR Patent No. 20190075097 A issued to Martin Breuil on Jun. 28, 2019 for Catheter devices for delivering mechanical pulses. However, it differs from the present invention because Breuil teaches a catheter device having an internal elongate hollow body extending between a proximal end and a distal end along a longitudinal axis, the elongate hollow body defining a longitudinal aperture extending between a proximal end and a distal end. An inner elongate hollow body molded and sized to receive a guide wire therein, and at least one mechanical waveguide secured to the inner elongated hollow body and extending longitudinally along at least a portion of the inner elongated hollow body, wherein the at least one mechanical waveguide is for propagating at least one mechanical wave, and at least one mechanical waveguide. In one embodiment, the catheter device described above may allow suction or blowing from gaps between mechanical waveguides. Aspiration may be used to remove debris generated by the catheter device, and blowing of the fluid may be used to deliver a fluid, such as a drug, to the target to be treated. In one embodiment, a drug (or similar) capsule may be located at the distal end of the bundle of mechanical waveguides, and the capsule may be triggered (released) from mechanical waves at the distal end of the device. In another embodiment, the catheter device further comprises an optical coherence tomography (OCT) or intravascular ultrasound (IVUS) imaging device between the catheter and the sleeve.

Applicant believes that another reference corresponds to WO Patent No. 2003/099100 A2 published to Zumeris, et al. on Nov. 11, 2004 for Method, apparatus and system for treating biofilms associated with catheters. However, it differs from the present invention because Zumeris, et al. teach an apparatus, system and method for preventing or treating biofilm associated with catheters. A piezo-ceramic element may be attached to a catheter and a vibration processor may be connected to the piezo-ceramic element. The vibration processor may provide electric signals that generate acoustic vibrations in the piezo-ceramic element, causing vibrations in or around the catheter. These vibrations may be particularly administered to disperse microbe colonies, thereby preventing or inhibiting formation of biofilm that may lead to infections. Vibrations may be amplified significantly due to resonance conditions in the catheter balloon, which may be powerful enough to be used to disperse microbe colonies that have grouped around the catheter or are attempting to do so.

Applicant believes that another reference corresponds to WO Patent No. 2009/152352 A2 published on Dec. 9, 2010 to Hawkins, et al. for Shockwave balloon catheter system. However, it differs from the present invention because Hawkins, et al. teach a system for breaking obstructions in body lumens that has a catheter including an elongated carrier, a balloon about the carrier in sealed relation thereto, the balloon being arranged to receive a fluid therein that inflates the balloon, and an arc generator including at least one electrode within the balloon that forms a mechanical shock wave within the balloon. The system further includes a power source that provides electrical energy to the arc generator.

Applicant believes that another reference corresponds to WO Patent No. 2018/014021 A2 published to Jiang et al. on Jan. 18, 2018 for Ultrasound transducer and array for intravascular thrombolysis. However, it differs from the present invention because Jiang et al. teach a catheter-implemented transducer device for intravascular thrombolysis. Such a transducer device includes a catheter defining a longitudinal axis and having opposed proximal and distal ends. At least one ultrasonic transducer arrangement is disposed about the distal end. The ultrasonic transducer arrangement is oriented with acoustic waves propagating parallel or perpendicular to the longitudinal axis. Optionally, the ultrasonic transducer arrangement is configured as a multi-layer stacked structure of ultrasonic transducer elements. Optionally, the ultrasonic transducer arrangement is a laser ultrasonic transducer arrangement. Optionally, the ultrasonic transducer arrangement is configured to operate in a lateral mode. Also, see pages 16-18.

Applicant believes that another reference corresponds to WO Patent No. 2018/083666 A1 published to Brouillette, et al. on May 11, 2018 for Device for delivering mechanical waves through a balloon catheter. However, it differs from the present invention because Brouillette, et al. teach a device for delivering mechanical waves to treat a lesion present in a blood vessel comprising a catheter extending between a first proximal end and a first distal end; an inflatable balloon secured to the catheter and being adjustable between an inflated configuration and a deflated configuration; and at least one mechanical waveguide extending between a second proximal end and a second distal end for propagating at least one mechanical wave from the second proximal end to the second distal, the mechanical waveguide being secured to the inflatable balloon or the catheter.

Applicant believes that another reference corresponds to WO Patent No. 2019/111239 A1 issued to Brouillette, et al. on Jun. 13, 2019 for Combined non-invasive and minimally-invasive mechanical energy targeting. However, it differs from the present invention because Brouillette, et al. teach a system for delivering mechanical waves to treat a lesion present in a vessel of a body comprising an external mechanical wave source for generating mechanical waves from outside of the body; and a wave directing device insertable in the vessel, the wave directing device for receiving the mechanical waves generated by the external mechanical wave source and redirecting the mechanical waves according to a target direction.

Other patents describing the closest subject matter provide for a number of more or less complicated features that fail to solve the problem in an efficient and economical way. None of these patents suggest the novel features of the present invention.

SUMMARY OF THE INVENTION

The present invention is a catheter for thromboembolic disease with mechanic waves, injection, and ejection comprising a triple-lumen catheter system having a first lumen for injection, a second lumen for ejection, and a third lumen having a mechanical wave emitter for wave emissions. The triple-lumen catheter system comprises a catheter body, a proximal end, and a distal end. The proximal end has connected a port assembly having an injection port, an ejection port, and an emission port. The first lumen, the second lumen, and the third lumen are longitudinal. The first lumen and the second lumen are approximately symmetric and opposite to each other. The first lumen and the second lumen are hollow. A first peripheral semicircular wall, a first interior semicircular wall, and first and second radial walls define the first lumen. The first peripheral semicircular wall and the first interior semicircular wall are concentric. A second peripheral semicircular wall, a second interior semicircular wall, and the first and second radial walls define the second lumen. The second peripheral semicircular wall and the second interior semicircular wall are concentric. The first interior semicircular wall and the second interior semicircular wall define the third lumen, whereby the third lumen is at center of the triple-lumen catheter system.

The mechanical wave emitter comprises first and second wires, and a horn unit. The mechanical wave emitter emits or releases sound waves. The mechanical wave emitter comprises the horn unit relatively adjacent to the distal end to release the sound waves into a blood vessel. The mechanical wave emitter is flexible. The first lumen is for injection of an anticoagulant solution into the blood vessels. The sound waves break up and/or destroy blood clots/thrombus. The second lumen is for ejection of residue and matter from the blood clots/thrombus and the anticoagulant solution. The injection, the ejection, and the waves emission are simultaneously.

It is therefore one of the main objects of the present invention to provide a catheter for thromboembolic disease with mechanic waves, injection, and ejection.

It is another object of this invention to provide a catheter for thromboembolic disease with mechanic waves, injection, and ejection wherein the mechanic waves are sound waves.

It is another object of this invention to provide a catheter for thromboembolic disease with mechanic waves, injection, and ejection that is volumetrically efficient for carrying, transporting, and storage.

It is another object of this invention to provide a catheter for thromboembolic disease with mechanic waves, injection, and ejection, which is of a durable and reliable construction.

It is yet another object of this invention to provide such a device that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE PREFERRED EMBODIMENT

Figure 1:
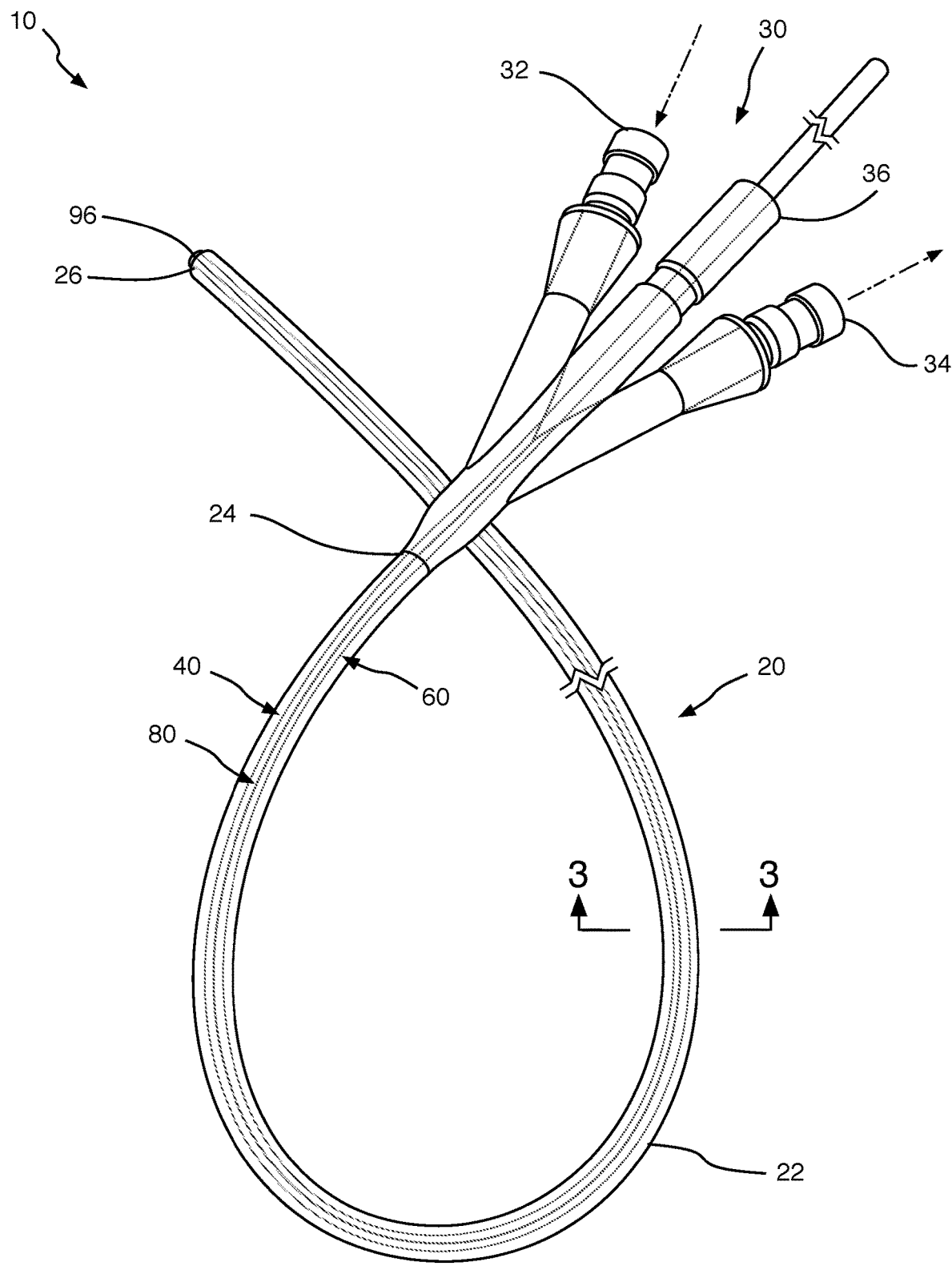
FIG. 1 is an isometric view of the present invention.

Referring now to the drawings, the present invention is a catheter for thromboembolic disease with mechanic waves, injection and ejection, and is generally referred to with numeral 10. It can be observed that it basically includes triple-lumen catheter system 20 having first lumen 40, second lumen 60, and third lumen 80.

Figure 2:
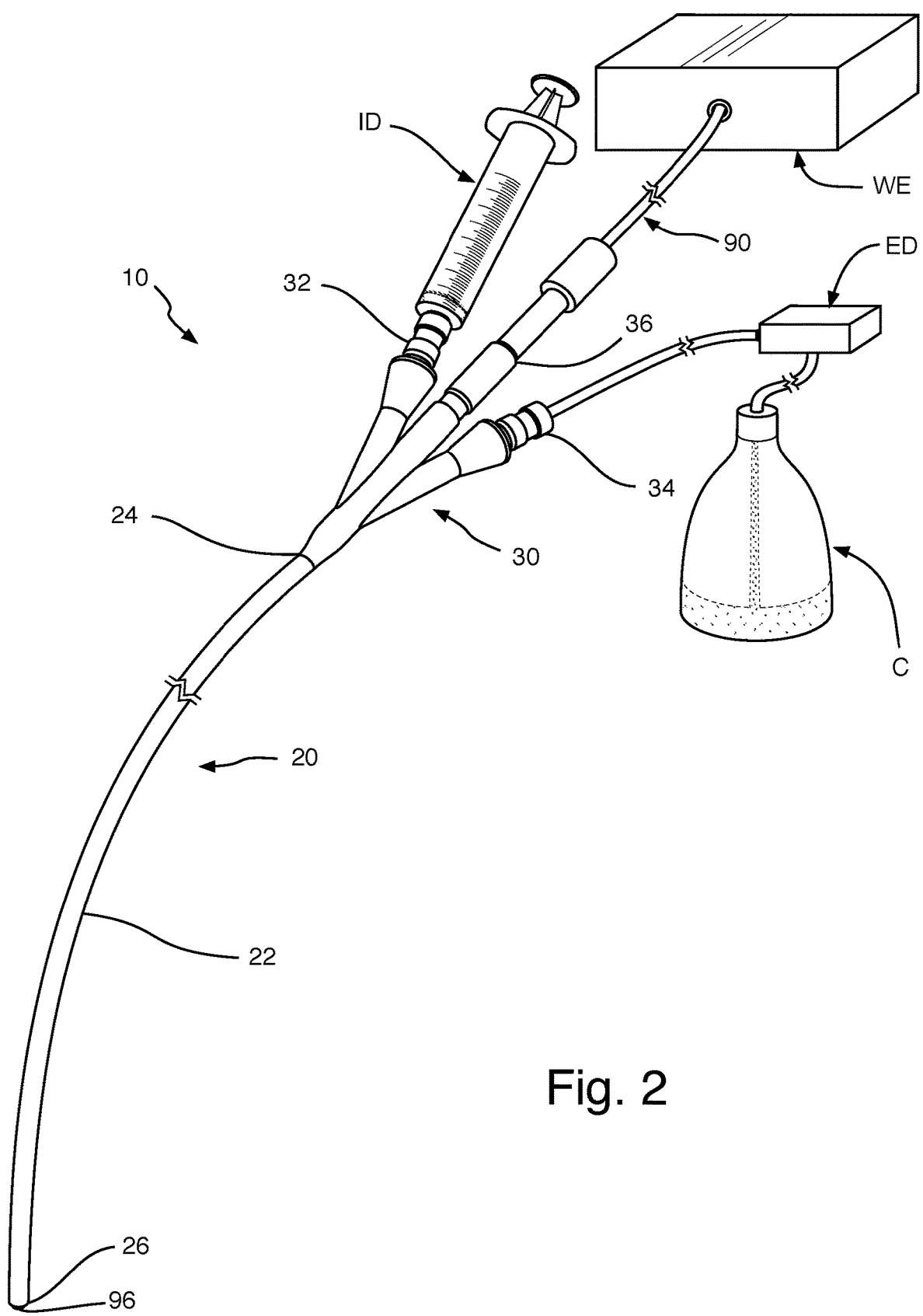
FIG. 2 is an isometric view of the present invention connected to respective injection device, ejection device, and wave emitter device.

As seen in FIGS. 1 and 2, triple-lumen catheter system 20 comprises catheter body 22, proximal end 24, and distal end 26. Proximal end 24 is connected to port assembly 30. First lumen 40, second lumen 60, and third lumen 80 are longitudinal. Port assembly 30 comprises injection port 32, ejection port 34, and emission port 36. Injection port 32 receives injection device ID and interconnects with first lumen 40. Ejection port 34 connects with ejection device ED having container C, and interconnects with second lumen 60. Emission port 36 is connected to wave emitter device WE, whereby mechanical wave emitter 90 passes through third lumen 80.

Figure 3:
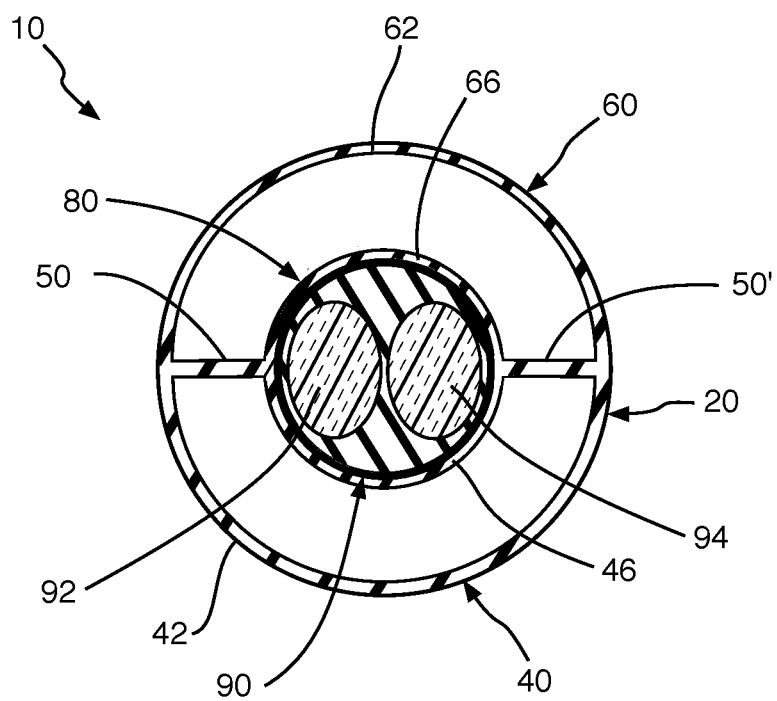
FIG. 3 is a cross-section view taken along lines 3-3 from FIG. 1.

As seen in FIG. 3, first peripheral semicircular wall 42, first interior semicircular wall 46, and first and second radial walls 50 and 50' define first lumen 40. First peripheral semicircular wall 42 and first interior semicircular wall 46 are concentric. Second peripheral semicircular wall 62, second interior semicircular wall 66, and first and second radial walls 50 and 50' define second lumen 60. Second peripheral semicircular wall 62 and second interior semicircular wall 66 are also concentric. First interior semicircular wall 46 and second interior semicircular wall 66 define third lumen 80 positioned approximately at a center of triple-lumen catheter system 20.

Figure 4:
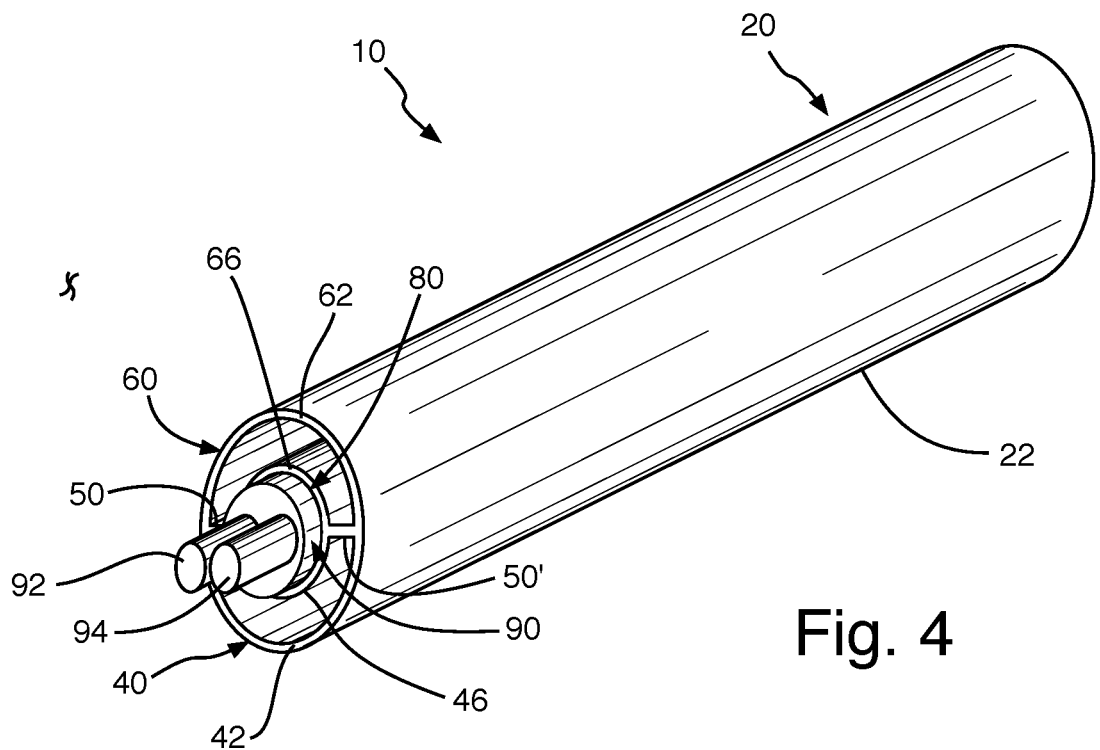
FIG. 4 is an isometric view of the present invention showing a mechanical wave emitter.

As seen in FIG. 4, first lumen 40 and second lumen 60 are symmetrical and opposite to each other. In a preferred embodiment, first lumen 40 and second lumen 60 are hollow. Mechanical wave emitter 90 comprises first and second wires 92 and 94, and horn unit 96, seen in FIGS. 1 and 2. Mechanical wave emitter 90 is flexible. In a preferred embodiment, mechanical wave emitter 90 emits or releases sound waves W as seen in FIGS. 5B, 5C, and 5D.

Figure 5A:
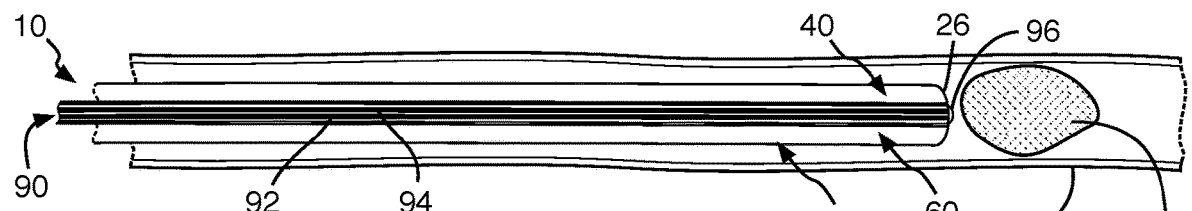
FIG. 5A is a cross-section view of the present invention presented into a blood vessel having a blood clot.

As seen in FIG. 5A, present invention 10 is inserted into blood vessel BV having blood clot/thrombus BC.

Figure 5B:
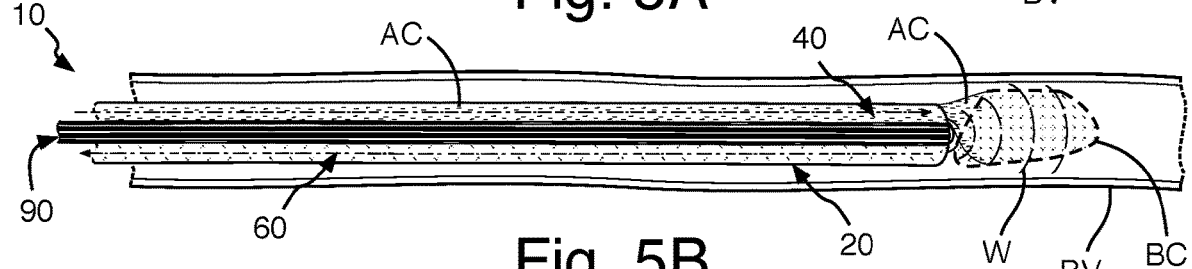
FIG. 5B is a cross-section view of the present invention presented into the blood vessel in a first stage of blood clot dissolution and ejection.

As seen in FIGS. 5A and 5B, triple-lumen catheter system 20 comprises first lumen 40 for injection, second lumen 60 for ejection, and third lumen 80, seen in FIGS. 3 and 4, that has mechanical wave emitter 90 to emit or release sound waves W into blood vessel BV. In a preferred embodiment, horn unit 96 slightly protrudes from distal end 26 to emit or release sound waves W.

Figure 5C:
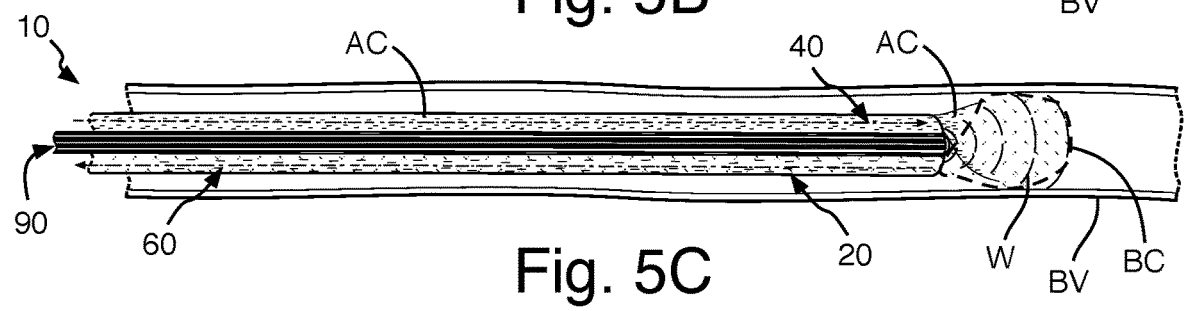
FIG. 5C is a cross-section view of the present invention presented into the blood vessel in a second stage of the blood clot dissolution and ejection.
Figure 5D:
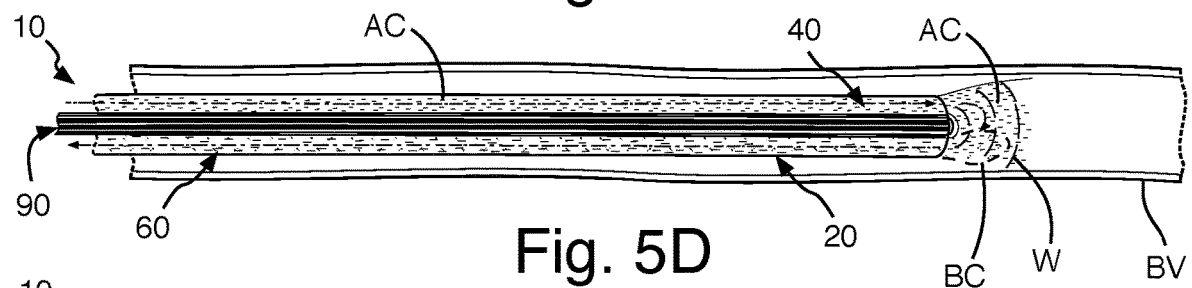
FIG. 5D is a cross-section view of the present invention presented into the blood vessel in a third stage of the blood clot dissolution and ejection.

As seen in FIGS. 5B, 5C, and 5D, first lumen 40 delivers anticoagulant solutions AC inside blood vessel BV, which has blood clot/thrombus BC, while mechanical wave emitter 90 emits or releases sound waves W onto blood clot/thrombus BC. Second lumen 60 is for ejection of residue and matter from blood clot/thrombus BC, and thrombus and anticoagulant solution AC. The injection, ejection, and emission of sound waves W occur approximately simultaneously.

As seen in FIGS. 5C and 5D, Sound waves W travel lengthwise to reach blood clot/thrombus BC, enhancing their impact with the help of anticoagulant solution AC injected through first lumen 40. Sound waves W increase a reaction speed between anticoagulant solution AC and blood clot/thrombus BC. Sound waves W propagate molecules with energy and velocities measurable within safe limits. In a preferred embodiment, sound wave frequencies used in present invention 10 are between 19 Hertz-19 Kilo Hertz. The wave frequency and sound wave energy may be graduated according to patient characteristics, but always between 19 Hertz-19 Kilo Hertz. Sound waves W and anticoagulant solution AC break up and destroy blood clot/thrombus BC and thrombus, typically in parts, while residue and matter from blood clot/thrombus BC, thrombus and anticoagulant solution AC are simultaneously removed/suctioned/extracted out from blood vessel BV through second lumen 60.

Figure 5E:
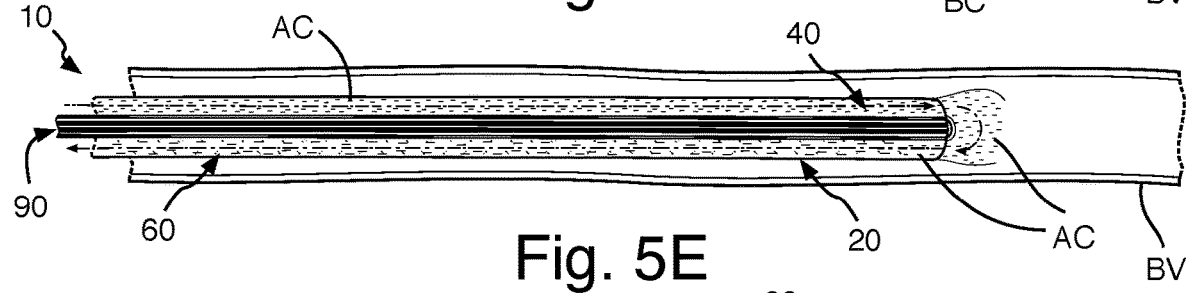
FIG. 5E is a cross-section view of the present invention presented into the blood vessel in a fourth stage of the blood clot dissolution and ejection.

As seen in FIGS. 5D and 5E, residue and matter from blood clot/thrombus BC, thrombus, and anticoagulant solution AC are removed/suctioned/extracted out once blood clot/thrombus BC is partially or totally broken up and/or destroyed. An ascendant spiral circulation is formed in front of blood clot/thrombus BC, removing/extracting the residue and matter of blood clot/thrombus BC out from blood vessel BV. This continues until blood clot/thrombus BC is completely broken up and/or destroyed and all the residue and matter is removed/suctioned/extracted from blood vessel BV.

Figure 5F:
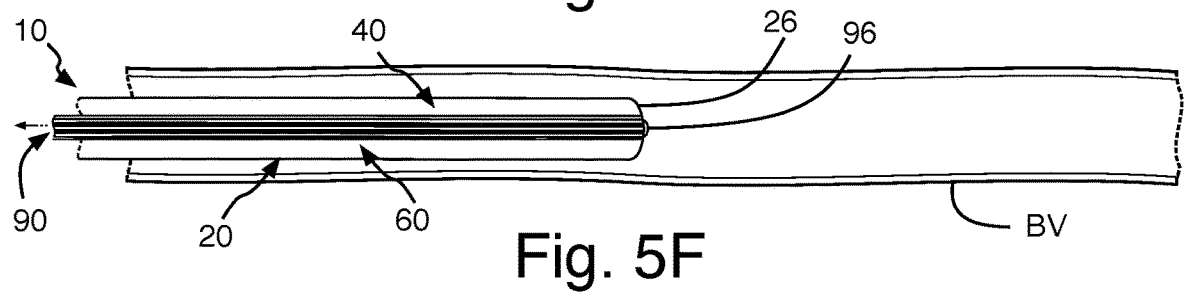
FIG. 5F is a cross-section view of the present invention presented into a blood vessel when the blood clot has been completely dissolved and ejected.

As seen in FIG. 5F, present invention 10 is then removed from blood vessel BV.

Present invention 10 may be used to treat thrombi pathologies of the circulatory system, especially pulmonary thrombi embolisms, coronary bifurcations, and periphery circulation problems in the legs. Present invention 10 breaks up and/or destroys cholesterol plates, clot, and/or thrombus in combination with injection and ejection.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A catheter system for treating thromboembolic disease with mechanical waves, injection, and ejection, comprising:
    a triple-lumen catheter having a first lumen for injection, a second lumen for ejection, and a third lumen having a mechanical wave emitter for waves emission,
    wherein said triple-lumen catheter comprises a catheter body, a proximal end, and a distal end, said proximal end has a port assembly connected thereto, said port assembly having an injection portion, an ejection port, and an emission port,
    wherein said mechanical wave emitter is flexible and comprises a horn unit and first and second wires, wherein said mechanical waver emitter emits or releases sound waves, and wherein said horn unit is protruding from said distal end and is configured to release said sound waves into a blood vessel,
    wherein said first lumen for injection is configured to inject an anticoagulant solution into said blood vessel, said first lumen is defined by a first peripheral semicircular wall, a first interior semicircular wall, and first and second radial walls, wherein said first peripheral semicircular wall and said first interior semicircular walls are concentric,
    wherein said second lumen is defined by a second peripheral semicircular wall, a second interior semicircular wall, and said first and second radial walls, wherein said second peripheral semicircular walls and second interior semicircular wall are concentric, and
    wherein said first interior semicircular wall and said second interior semicircular wall define said third lumen, said third lumen is approximately positioned at a center of said triple-lumen catheter, wherein said third lumen for mechanical wave emissions is surrounded by said first and second semicircular lumens.

2. The catheter system for treating thromboembolic disease with mechanical waves, injection, and ejection set forth in claim 1, further characterized in that said first lumen, said second lumen, and said third lumen are longitudinal.

3. The catheter system for treating thromboembolic disease with mechanical waves, injection, and ejection set forth in claim 1, further characterized in that said first lumen and said second lumen are symmetrical and opposite to each other.

4. The catheter system for treating thromboembolic disease with mechanical waves, injection, and ejection set forth in claim 1, further characterized in that said first lumen and said second lumen are hollow.

5. The catheter system for treating thromboembolic disease with mechanical waves, injection, and ejection set forth in claim 1, further characterized in that said sound waves are configured to break up and/or destroy a blood clot/thrombus.

6. The catheter system for treating thromboembolic disease with mechanical waves, injection, and ejection set forth in claim 5, further characterized in that said second lumen is configured for ejection of residue and matter from said blood clot/thrombus and said anticoagulant solution.

7. The catheter system for treating thromboembolic disease with mechanical waves, injection, and ejection set forth in claim 5, further characterized in that said first lumen for injection, said mechanical wave emitter and said second lumen for ejection are configured to simultaneously destroy, suction and extract out said blood clot/thrombus from a blood vessel.

8. The catheter system for treating thromboembolic disease with mechanical waves, injection, and ejection set forth in claim 7, further characterized in that said sound waves have a frequency between 19 Hertz-19 Kilo Hertz.

* * * * *